US006176858B1

United States Patent
Dequesne et al.

(10) Patent No.: US 6,176,858 B1
(45) Date of Patent: Jan. 23, 2001

(54) ELECTROSURGICAL LOOP AND INSTRUMENT FOR LAPAROSCOPIC SURGERY

(75) Inventors: Jacques Dequesne, Lausanne (CH); Camille Constant; Xavier Moreels, both of Gembloux (BE)

(73) Assignee: Medsys S.A., Gembloux (BE)

( * ) Notice: Under 35 U.S.C. 154(b), the term of this patent shall be extended for 0 days.

(21) Appl. No.: 09/240,408

(22) Filed: Jan. 29, 1999

Related U.S. Application Data

(63) Continuation of application No. 60/109,767, filed on Nov. 25, 1998, which is a continuation of application No. 60/112,308, filed on Dec. 14, 1998.

(51) Int. Cl.[7] ................................................. A61B 18/18
(52) U.S. Cl. ............................... 606/47; 606/45; 606/48; 606/113
(58) Field of Search ............................. 606/32, 41, 47, 606/48, 50, 113, 114

(56) References Cited

U.S. PATENT DOCUMENTS

| 4,493,320 | * | 1/1985 | Treat ....................................... 606/47 |
| 5,078,716 | * | 1/1992 | Doll ....................................... 606/47 |
| 5,158,561 | * | 10/1992 | Rydell et al. ......................... 606/113 |
| 5,318,564 | * | 6/1994 | Eggers .................................... 606/47 |
| 5,437,665 | * | 8/1995 | Munro .................................... 606/47 |
| 5,782,839 | * | 7/1998 | Hart et al. ............................ 606/113 |
| 5,860,987 | * | 1/1999 | Ratcliff et al. ....................... 606/113 |
| 5,971,994 | * | 10/1999 | Fritzsch ................................ 606/113 |

FOREIGN PATENT DOCUMENTS

| 0 041 719 B1 | 5/1984 | (EP) . |
| WO 93/24062 | 12/1993 | (US) . |

* cited by examiner

Primary Examiner—Linda C. M. Dvorak
Assistant Examiner—David M. Ruddy
(74) Attorney, Agent, or Firm—Knobbe, Martens, Olson & Bear, LLP

(57) ABSTRACT

An electrosurgical cutting apparatus for performing laparoscopic section of an organ makes use of an electrical current transporter. The transporter includes a conducting wire, electrical insulation portions around the conducting wire at the first end and at the second end, forming respectively a first and a second insulated end and defining a non-insulated cutting portion between said first insulated end and said second insulated end, and a first fastening device located at the first end of the conducting wire and a second fastening device located at the second end of said conducting wire. The second fastening device is in electrical contact with the conducting wire.

20 Claims, 7 Drawing Sheets

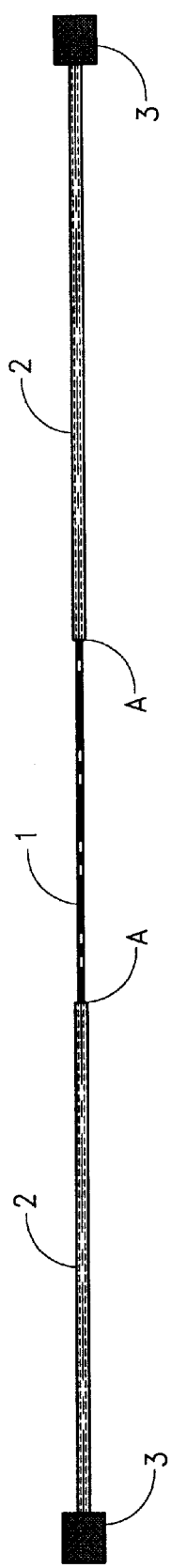
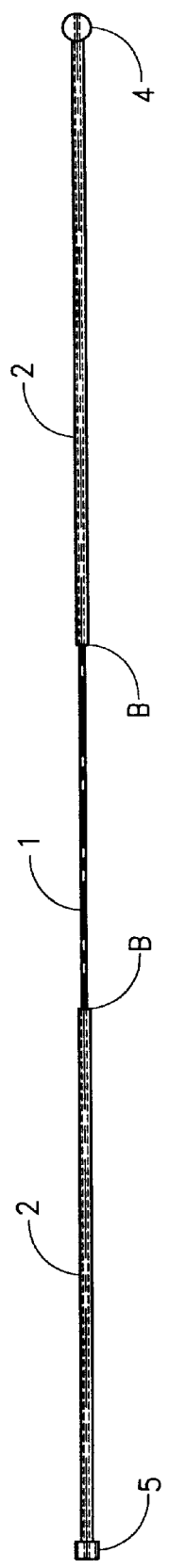
FIG. 1
FIG. 2

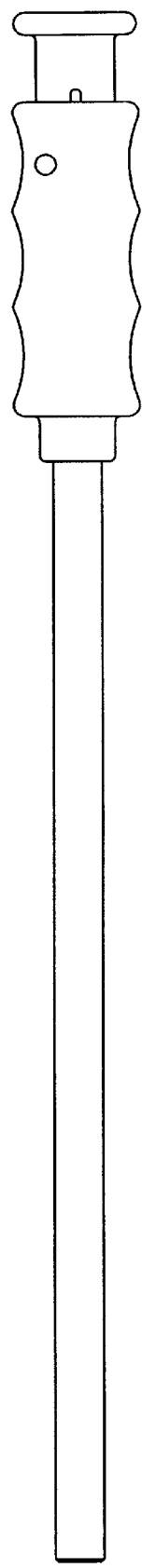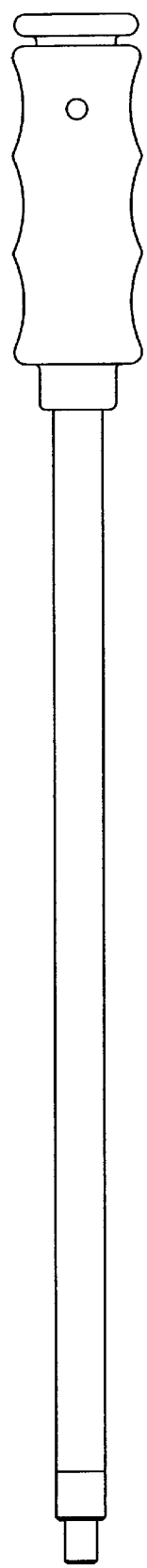
FIG. 5A
FIG. 5B

ELECTROSURGICAL LOOP AND INSTRUMENT FOR LAPAROSCOPIC SURGERY

RELATED APPLICATIONS

This application claims priority under 35 U.S.C. §119(e) from Provisional Application Nos. 60/109,767 and 60/112,308 filed Nov. 25, 1998 and Dec. 14, 1998, respectively.

FIELD OF THE INVENTION

This invention relates to surgical instruments, and more particularly to electrosurgical instruments for laparoscopic surgery.

The invention further relates to a laparoscopic method for performing a section of an organ using an electrosurgical instrument.

STATE OF HTE ART

Supracervical or subtotal hysterectomy is a procedure in which there is renewed interest, and it is currently being evaluated in patients presenting with benign uterine disease and a healthy cervix. The technique of Laparoscopic Supracervical Hysterectomy (LSH) has only been introduced recently (Semm, K. Hysterectomy via laparotomy or pelviscopy. A new CASH method without colpotomy, *Geburtshilfe und Frauenheilkunde,* 1991; 51: 996–1003; Pelosi, M. A., Pelosi, M. A. III. Laparoscopic supracervical hysterectomy using a single-umbilical puncture (mini-laparoscopy), *Journal of Reproductive Medicine,* 1992; 37: 777–784; Donnez J., Nisolle M. LASH, Laparoscopic supracervical (subtotal) hysterectomy, *Journal of Gynaecologic Surgery,* 1993; 9: 92–94.)

Some of the potential advantages of this procedure include a shorter operation time, fewer complications and an earlier return to normal activity including sexual function.

A difficult part of the laparoscopic procedure is the sectioning of the uterine cervix. Conditions are often far from optimal due to the angle of approach with the cutting electrode or scissors and the proximity of neighbouring important structures such that are sometimes difficult to keep at a distance. Safety has always been an important consideration when choosing a supracervical procedure rather than a total hysterectomy. By avoiding the risk of cervical dissection with possible ureteral lesions, the complication rate may be reduced with a supracervical technique. However, when cutting the cervix with any monopolar instrument, there is an associated risk of damaging adjacent structures.

AIMS OF THE INVENTION

A first aim of the present invention is to provide a new surgical instrument for performing laparoscopic section of an organ.

A further aim of the present invention is to provide a new surgical instrument that reduces operation time when performing a laparoscopic supracervical hysterectomy or a total laparoscopic hysterectomy.

Another aim of the present invention is to provide a new method for performing a laparoscopic section of an organ, a laparoscopic supracervical hysterectomy or a total laparoscopic hysterectomy.

SUMMARY OF THE INVENTION

The present invention relates to an electrosurgical cutting apparatus for performing laparoscopic section of an organ, comprising an electrical current transporter, said transporter comprising:

A conducting wire electrical insulation portions around said conducting wire at the first end and at the second end, forming respectively a first and a second insulated end and defining a non-insulated cutting portion between said first insulated end and said second insulated end, and a first fastening device located at said first end of said conducting wire and a second fastening device located at said second end of said conducting wire, said second fastening device being in electrical contact with said conducting wire.

Preferably, the electrical insulation portions comprise Teflon® and/or medical grade thermoretractable polyolefine.

The conducting wire preferably comprises a metal, said metal being advantageously selected from the group consisting of tungsten and stainless steel.

The conducting wire preferably has a length between 10 and 20 cm.

In a first embodiment of the present invention, the first fastening device and the second fastening device are clips adapted to be held by a standard laparoscopic forceps. In this case, the electrosurgical cutting apparatus of the embodiment described hereabove further comprises an insulating tube of at least the same length as the conducting wire, and which is broad enough to fit a standard laparoscopic forceps.

In a second embodiment of the present invention, the first fastening device is a screw or the like and the second fastening device is a conducting sphere or the like. Preferably, the screw or the like is insulated. Preferably, the electrosurgical cutting apparatus of the second embodiment described hereabove further comprises:

an introducer device comprising a rod having a proximal end and a distal end, said rod having at its distal end a screwhole adapted to retain said screw or the like and a groove adapted to fit and electrically contact said conducting sphere or the like, said rod having at its proximal end an insulated handle, a contact and an insulated spring therebetween, said contact being in electrical contact with said groove, and an insulated sheath having a length that is greater than the length of the wire and lesser than the length of said introducer device and comprising a tube and a handle, both adapted to fit the introducer, said handle comprising a plug and a contactor mechanism being in electrical contact with each other, said contactor mechanism not being in contact with the contact of the introducer when the introducer is inserted in the sheath and the distal end extends beyond the sheath, and being in contact with the contact of the introducer when the introducer is in a retracted position such that the distal end is inside the sheath, so that the wire and the plug are electrically connected. Preferably, the electrosurgical cutting apparatus as in this second embodiment further comprises a pin located on the handle of the introducer and a second groove located inside the handle of the sheath, said second groove being adapted to fit said pin and to prohibit translational movement of the introducer with respect to the sheath by trapping said pin when introducer and sheath are rotated with respect to each other.

A third embodiment of the present invention is an electrosurgical cutting apparatus as described hereabove as the second embodiment, further comprising:

an introducer device comprising a rod having a proximal end and a distal end, said rod having at its distal end a screwhole adapted to retain said screw or the like and a groove adapted to fit and electrically contact said conducting sphere or the like, said rod having at its proximal end an insulated handle, an electrical plug and an insulated spring, said electrical plug being in electrical contact with said groove, and an insulated sheath having a length that is greater than the length of the wire and lesser than the length of said introducer device and comprising a tube and a handle, both adapted to fit the introducer.

Preferably, the electrosurgical cutting apparatus as described in the third embodiment hereabove further comprises a pin located inside the handle of the sheath and a second groove located on the handle of the introducer, said second groove being adapted to fit said pin and to prohibit translational movement of the introducer with respect to the sheath by trapping said pin when introducer and sheath are rotated with respect to each other.

Another aspect of the present invention is a method for performing a laparoscopic section of an organ using an electrosurgical cutting apparatus as described in the first embodiment of the present invention, comprising the following steps:

grasping one clip of the apparatus with a first standard laparoscopic forceps, introducing said forceps and apparatus into a patient's body through a trocar, grasping the second clip of the apparatus with a second standard forceps and placing the conducting wire around the organ to be sectioned, grasping the second clip with the first standard forceps, and applying high frequency monopolar current to said conducting wire while performing a lateral traction on the apparatus with the first standard forceps.

Prior to the introduction of forceps and apparatus into a patient's body through a trocar, the apparatus is preferably inserted in an insulating tube to insulate the apparatus from the trocar. The organ to be sectioned is preferably an uterus, the operation being a Laparoscopic Assisted Supracervical Hysterectomy or a Total Laparoscopic Hysterectomy.

Another aspect of the present invention is a method for performing a laparoscopic section of an organ using an electrosurgical cutting apparatus as described in the second or third embodiment of the present invention, comprising the following steps:

introducing the introducer maximally into the sheath, so that the distal end of the introducer extends beyond the sheath, screwing the screw into the screwhole, pulling the introducer out of the sheath until the wire is completely inside the sheath, introducing said sheath into a patient's body through a trocar, re-introducing the introducer maximally into the sheath, so that the distal end of the introducer extends beyond the sheath and the wire and distal end are in the peritoneal cavity, grasping the sphere of the apparatus with a standard forceps and placing the wire around the organ to be sectioned, introducing the sphere into the groove of the introducer and retracting the introducer until the distal end is inside the sheath, thus preventing the sphere to be released from the groove, rotating the introducer so that introducer and sheath are fixed, and applying high frequency monopolar current to said wire while performing a lateral traction on the apparatus with the introducer and sheath.

The organ to be sectioned is an uterus, the operation being a Laparoscopic Assisted Supracervical Hysterectomy or a Total Laparoscopic Hysterectomy.

SHORT DESCRIPTION OF THE DRAWINGS

FIG. 1 draws a LEC electrosurgical loop according to the present invention.

FIG. 2 depicts a LAP electrosurgical loop according to the present invention.

FIG. 5 describes a combined sheath and introducer according to the present invention.

Figure 3A:
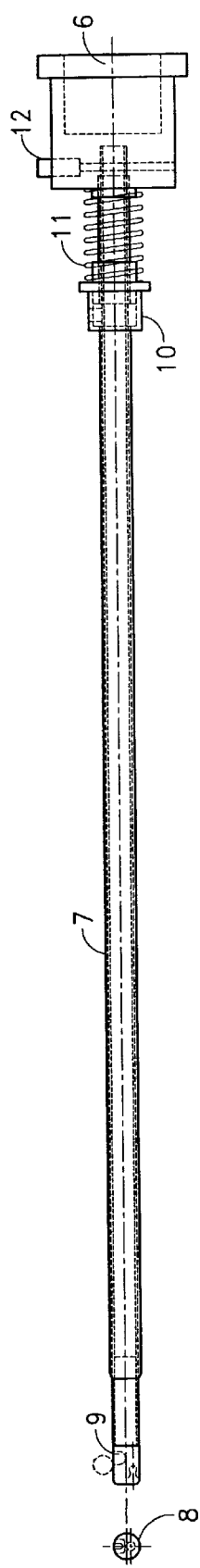
FIGS. 3A and 3C represent an introducer according to an embodiment of the present invention in a top view and a side view.
Figure 3B:
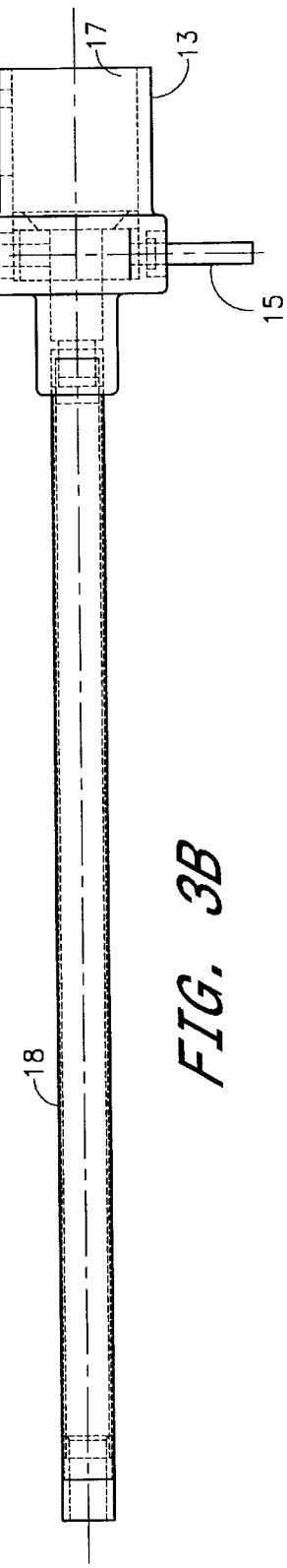
FIGS. 3B and 3D show a sheath according to an embodiment of the present invention in a top view and a side view.
Figure 3C:
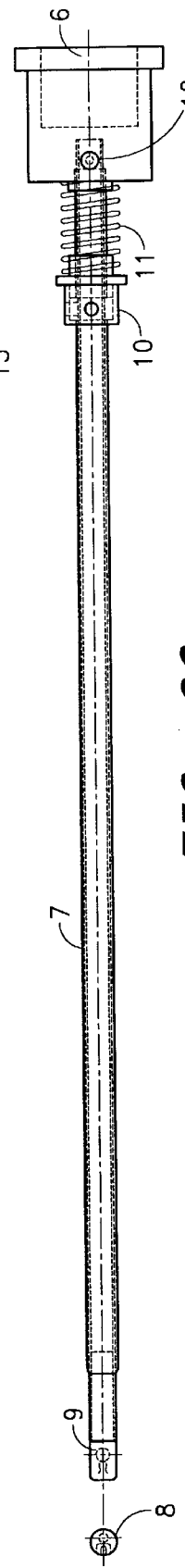
Figure 3D:
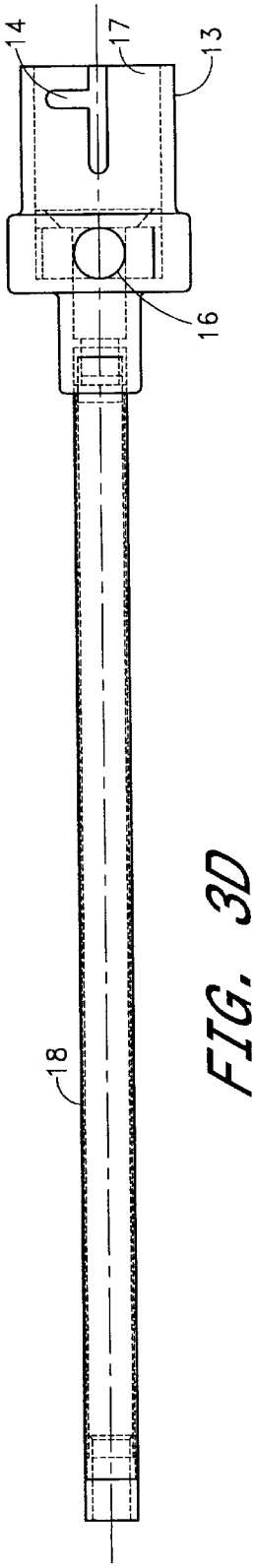
Figure 4A:
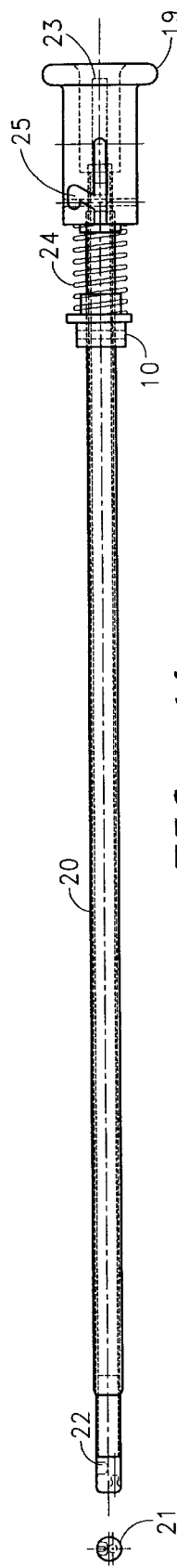
FIGS. 4A and 4C represent an introducer according to another embodiment of the present invention in a top view and a side view.
Figure 4B:
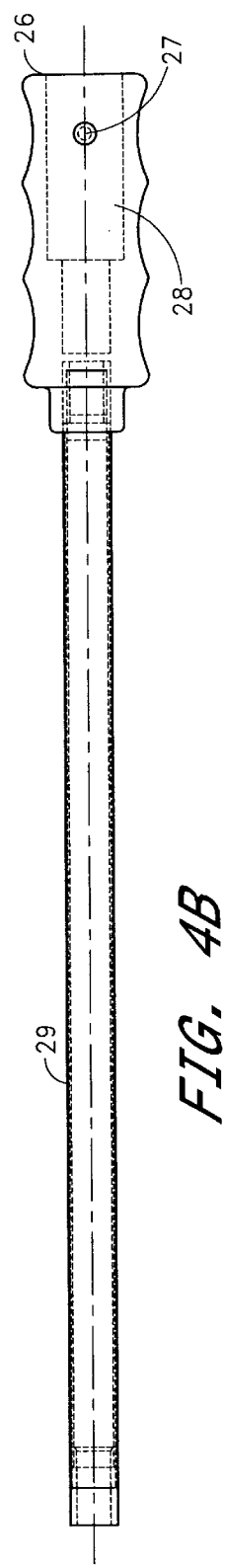
FIGS. 4B and 4D show a sheath according to another embodiment of the present invention in a top view and a side view.
Figure 4C:
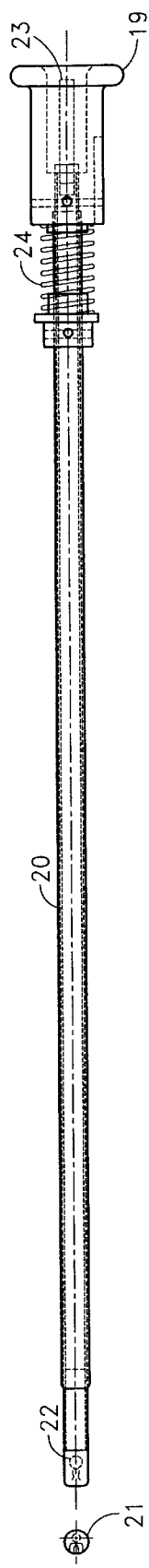
Figure 4D:
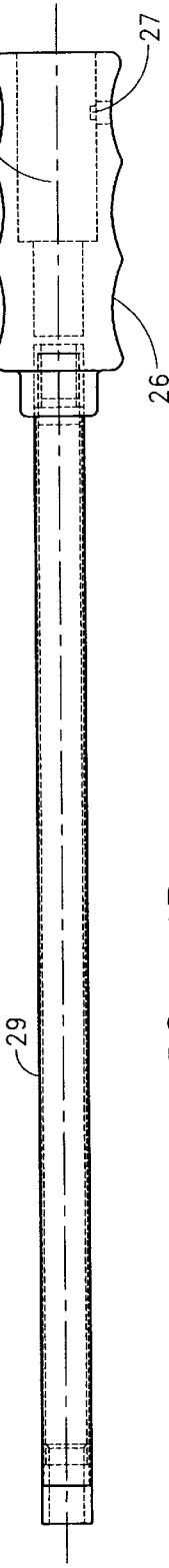
Figure 6:
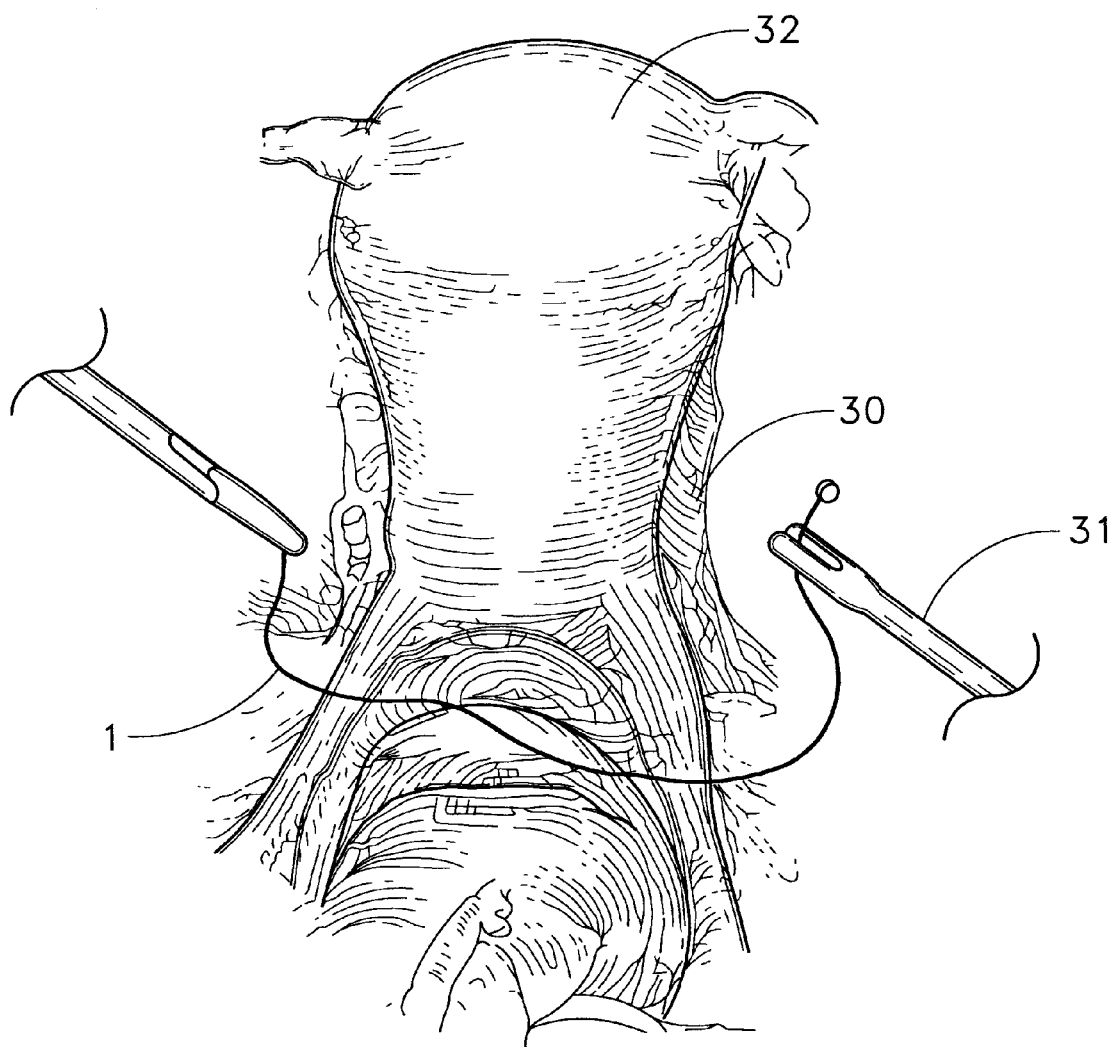

FIG. 6 shows the placement of an electrosurgical loop according to the present invention around the uterine cervix at the level of the isthmus.

Figure 7:
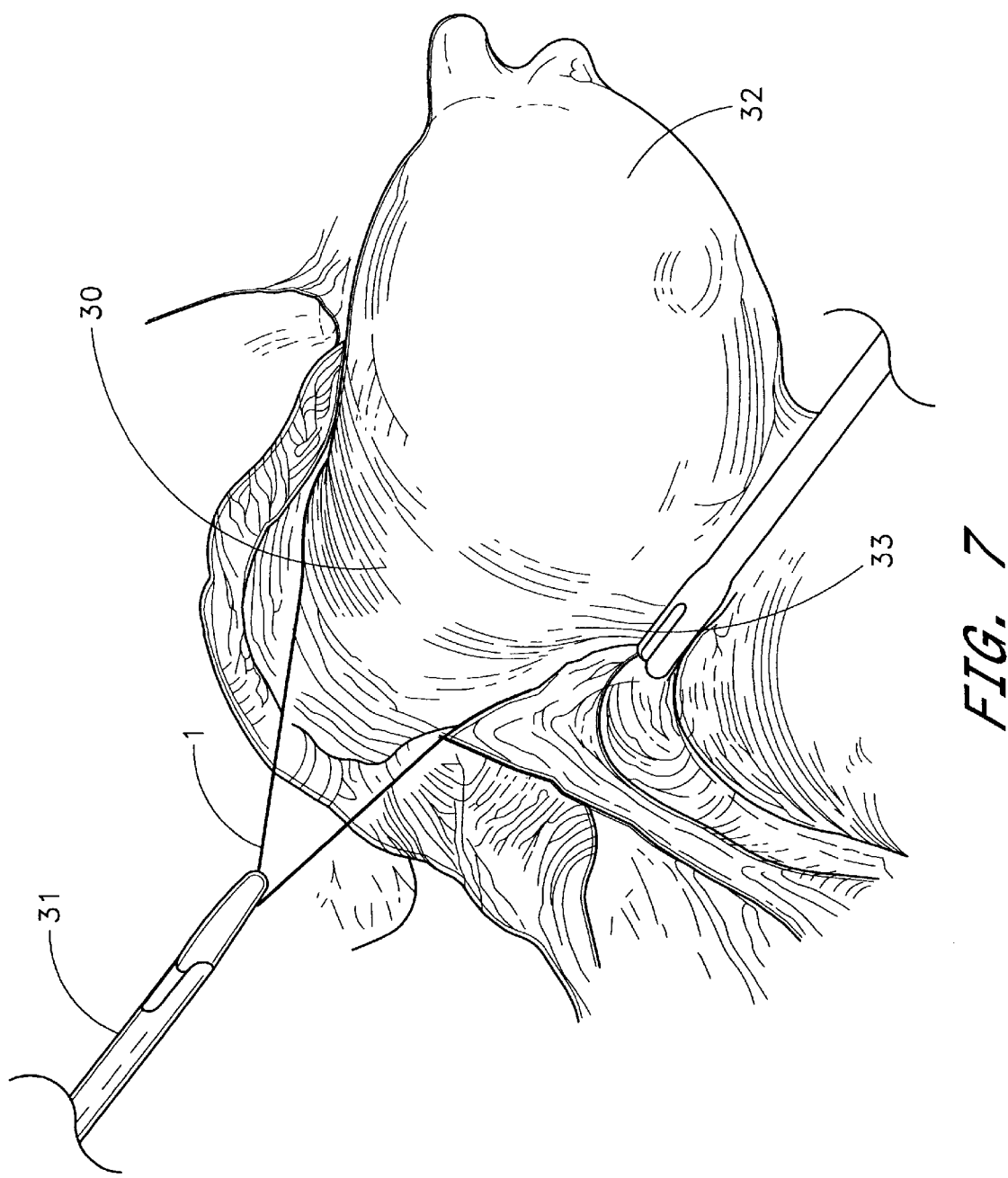

FIG. 7 describes the cutting of the cervix by applying monopolar current on the electrosurgical loop according to the invention while performing lateral traction on the loop.

Figure 8:
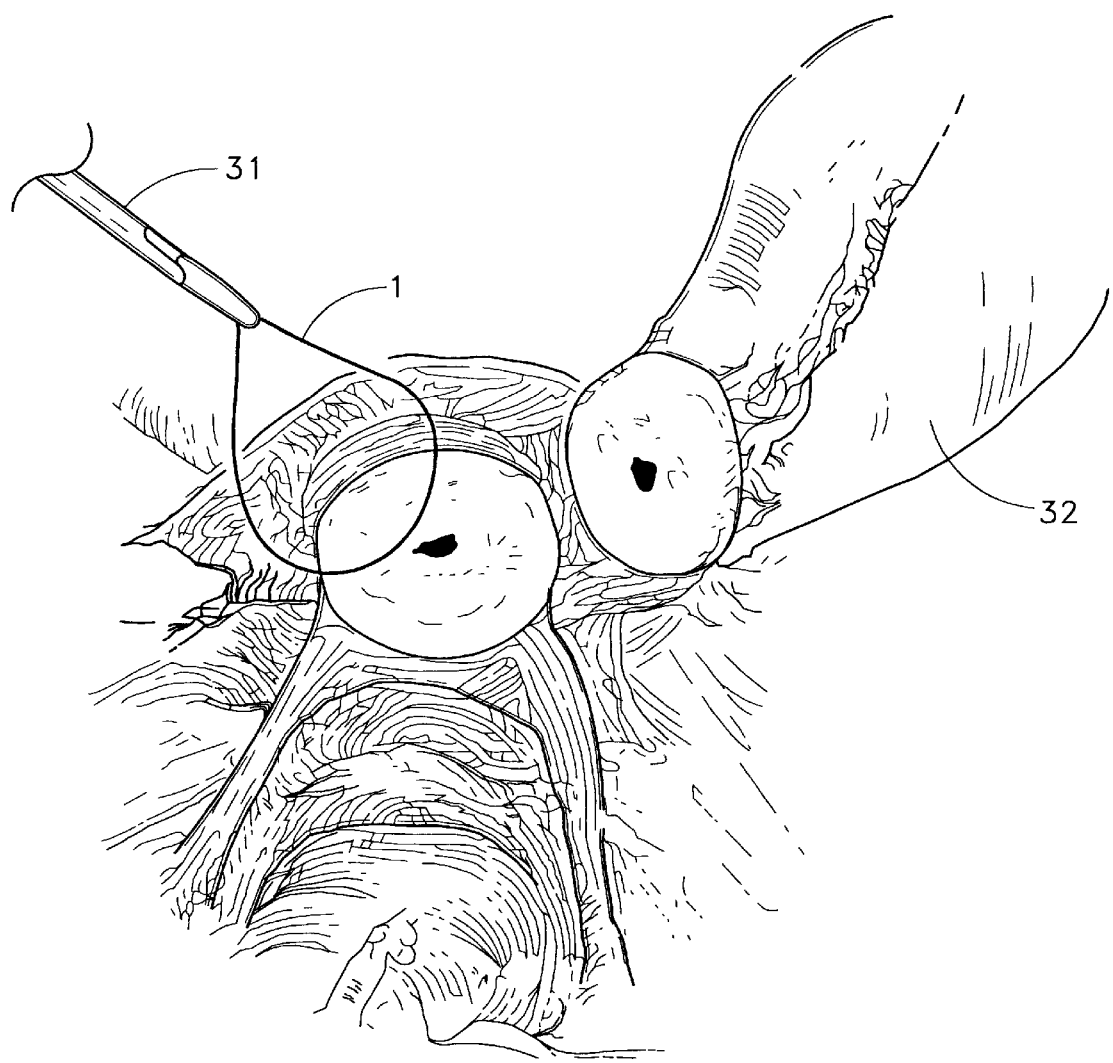

FIG. 8 presents a view of the cervical stump while the uterine corpus is displaced.

DETAILED DESCRIPTION OF THE INVENTION

The present invention concerns a new electrosurgical instrument for performing laparoscopic section of organs, in particular for performing a laparoscopic supracervical hysterectomy or a total laparoscopic hysterectomy, as well as a novel method for performing laparoscopic section of organs, in particular for performing a laparoscopic supracervical hysterectomy or a total laparoscopic hysterectomy.

The present invention will now be further clarified using examples that are non-limiting for the scope of the invention.

The electrosurgical instrument according to a specific embodiment of the present invention (the LEC loop) is meant to be used with the standard laparoscopic grasping forceps instrument, as described in FIGS. 6, 7 and 8.

EXAMPLE 1

The LEC Loop and Insulating Tube

The LEC loop can be seen in FIG. 1. It comprises a metal wire 1 that is covered on both ends with an insulating polymer 2 as Teflon® or thermoretractable polyolefine (medical grade). The metal wire 1 is not covered in between both insulating polymer layers 2 and thus a conducting part (A–A') is freely contactable and usable for electrosurgical purposes. Said metal wire is preferably made of stainless steel or tungsten. The ends of the wire are connected to and in electrical contact with clips 3, which enable the surgeon to manipulate the LEC loop using a standard laparoscopic forceps.

The LEC loop is used in co-operation with an insulated tube. Said tube is a 10 mm wide tube with a 5 mm reductor that is introduced in the non-insulated surgical trocar. The length of the tube should be enough for it to contain the full length LEC loop wire, thus insulating the LEC loop from the trocar.

EXAMPLE 2

Use of the LEC Loop

One introduces the laparoscopic grasping forceps through the insulating tube and grasps one end of the LEC loop. The forceps is then pulled back until the loop is entirely introduced in the insulating tube. The tube is then inserted in the peritoneal cavity through the trocar. The forceps is pushed until the loop is entirely pushed out of the insulating tube into the peritoneal cavity. The LEC loop can then be positioned around the organ that needs to be sectioned with the help of a second forceps that can hold the second end of the LEC loop. The second forceps is inserted through a second trocar.

The second end of the LEC loop is then directed to the first laparoscopic forceps and connected hereto by grasping the clip at the second end. Closing of the jaws of the forceps and retracting said forceps through the insulating tube permits to hide the freely contactable clips at the peripheral ends of the LEC loop inside the insulating tube and, when executing a lateral traction to the LEC loop while applying a high-frequency monopolar current to the LEC loop, the organ will be sectioned.

EXAMPLE 3

The LAP Loop

The LAP loop can be seen in FIG. 2. It comprises a metal wire 1 that is covered on both ends with an insulating polymer 2 as Teflon® or thermoretractable polyolefine (medical grade). The metal wire 1 is not covered in between both insulating polymer layers 2 and thus a conducting part (B–B') is freely contactable and usable for electrosurgical purposes. Said metal wire is preferably made of stainless steel or tungsten. One end of the wire is connected to and in electrical contact with a metal sphere 4, while the second end of the wire is connected to a screw 5, preferably being at least covered with an electrically insulating material as Teflon®. The metal sphere 4 can be replaced by another geometrical form, which can be clamped inside a groove in the lap loop instrument adapted to retain the form. Further, the screw can be replaced by any fixation means, compatible with the lap loop instruments.

EXAMPLE 4

A First Version of LAP Loop Instruments

The first version of LAP loop instruments can be seen in FIG. 3. FIGS. 3A and 3C represent a LAP introducer instrument. FIGS. 3B and 3D represent a LAP sheath instrument.

The LAP introducer instrument comprises an electrically insulated handle 6 connected to an insulated rod 7, comprising at its distal end a threaded hole 8 or the like adapted to fit the screw 5 or the like of the LAP loop and a groove 9 adapted to receive the sphere 4 or the like of the LAP loop. Said groove is in electrical contact with a contact 10, located at the proximal part of said rod 7. Also at the proximal part of said rod 7 near said insulated handle 6, there is an electrically insulated spring 11. The insulated handle comprises preferably a pin 12

The LAP sheath instrument comprises a handle 13 comprising a second groove 14, adapted to fit pin 12, an electrical plug 15, which is in electrical contact with a contactor mechanism 16 and an opening 17 adapted to receive the introducer handle.

Further, the LAP sheath instrument comprises an insulating tube 18, that is adapted to receive the rod 7, but having a reduced length so that, when the introducer is pushed in to the sheath as far as possible, the distal end of the rod 7 is outside of the insulating tube 16. The handle 13 is adapted so that, in this introducer position, the contactor mechanism 16 can only contact the insulated spring 11 of said introducer.

When the introducer is retracted so that rod 7 is completely inside insulating tube 18, the contactor mechanism 16 is, when depressed, in contact with the contact 10 of the introducer, thus achieving electrical contact between the plug 15 of the sheath and the groove 9 of the introducer, and the wire 1 of the LAP loop when the sphere 4 is inside the groove 9. Preferably, the contact 10 is adapted to fix the contactor mechanism 16 when this position is taken. A rotation of the introducer with regard to the sheath in this position will fix the introducer more rigidly, as the pin 12 of the introducer will end up in the side-arm of second groove 14 of the sheath, thereby excluding further translational movement of the introducer inside the sheath.

EXAMPLE 5

Use of the LAP Loop and First Version of the LAP Loop Instruments

One introduces the introducer through the insulating tube 18 of the sheath until the rod 7 is maximally inserted (the distal end extends beyond the insulating tube 18). In this position, the contact mechanism 16 can not contract the contact 10 of the introducer. The LAP loop is screwed on the distal end of the introducer with its screw 5. The introducer is then retracted, which allows the distal end to enter the insulating tube 18 again. The introducer is then pulled back until the LAP loop is entirely introduced in the insulating tube. The sheath is then inserted in the peritoneal cavity trough the trocar. The introducer is again pushed until the LAP loop is entirely pushed out of the insulating tube 18 into the peritoneal cavity until maximal insertion (insulated spring 11 compressed). In this position, no electrical contact is possible between the distal end of the introducer and the plug 15 of the sheath. The LAP loop can then be positioned around the organ that needs to be sectioned with the help of a forceps that can hold the second end of the LAP loop. The forceps is inserted through a second trocar.

The sphere 4 of the LAP loop is then directed to the distal end of the introducer and placed into the groove 9 at said distal end. Retraction of the introducer until the distal end of the introducer is completely inside the insulating tube is followed by a rotation resulting in fixation of the pin 12 in the side-arm of second groove 14.

The insulating tube prevents, in this position, the sphere 4 of the LAP loop to move since it is fixed in the groove 9 of the introducer, while the wire 1 of the LAP loop is in electrical contact with the plug 15 of the sheath via the contactor mechanism 16.

When executing a lateral traction to the LAP loop while applying a high-frequency monopolar current to the LAP loop, the organ will be sectioned.

The LAP loop and LAP loop instruments provide higher safety, since a closed electrical circuit is only possible when both ends of the loop are installed and the distal end of the introducer is hidden by the insulating tube.

EXAMPLE 6

A Second Version of LAP Loop Instruments

The second version of LAP loop instruments can be seen in FIG. 4. FIGS. 4A and 4C represent a LAP introducer instrument. FIGS. 4B and 4D represent a LAP sheath instrument.

The LAP introducer instrument comprises an electrically insulated handle 19 connected to an insulated rod 20, comprising at its distal end a threaded hole 21 or the like adapted to fit the screw 5 or the like of the LAP loop and a groove 22 adapted to receive the sphere 4 or the like of the LAP loop. Said groove is in electrical contact with an electrical plug 23, located inside handle 19. Also, at the proximal part of said rod 20 near said insulated handle 19, there is an electrically insulated spring 24. The insulated handle comprises a second groove 25, adapted to fit the pin . . . of the sheath.

The LAP sheath instrument comprises a handle 26 comprising a pin 27 and an opening 28 adapted to receive the introducer handle.

Further, the LAP sheath instrument comprises an insulating tube 29, that is adapted to receive the rod 20, but having a reduced length so that, when the introducer is pushed in to the sheath as far as possible, the distal end of the rod 20 is outside of the insulating tube 29, as can be seen in FIG. 5B.

When the introducer is retracted so that rod 20 is completely inside insulating tube 29, the introducer can be rotated with regard to the sheath which will fix the introducer more rigidly, as the pin 27 of the sheath will end up in the side-arm of second groove 25 of the introducer, thereby excluding further translational movement of the introducer inside the sheath. The introducer and sheath are then in the position as can be seen in FIG. 5A.

EXAMPLE 7

Use of the LAP Loop and Second Version of the LAP Loop Instruments

One introduces the introducer through the insulating tube 29 of the sheath until the rod 20 is maximally inserted (the distal end extends beyond the insulating tube 29). The LAP loop is screwed on the distal end of the introducer with its screw 5. The introducer is then retracted, which allows the distal end to enter the insulating tube 29 again. The introducer is then pulled back until the LAP loop is entirely introduced in the insulating tube. The sheath is then inserted in the peritoneal cavity through the trocar. The introducer is again pushed until the LAP loop is entirely pushed out of the insulating tube 29 into the peritoneal cavity until maximal insertion (insulated spring 24 compressed). The LAP loop can then be positioned around the organ that needs to be sectioned with the help of a forceps that can hold the second end of the LAP loop. The forceps is inserted through a second trocar.

The sphere 4 of the LAP loop is then directed to the distal end of the introducer and placed into the groove 22 at said distal end. Retraction of the introducer until the distal end of the introducer is completely inside the insulating tube is followed by a rotation resulting in fixation of the pin 27 in the side-arm of second groove 25.

The insulating tube 29 prevents, in this position, the sphere 4 of the LAP loop to move since it is fixed in the groove 22 of the introducer, while the wire 1 of the LAP loop is in electrical contact with the plug 23 of the sheath.

When executing a lateral traction to the LAP loop while applying a high-frequency monopolar current to the LAP loop, the organ will be sectioned.

EXAMPLE 8

Example of a Laparoscopic Supracervical Hysterectomy (LSH) According to the Present Invention Preparation for LSH includes placement of a uterine manipulator and catheterisation of the bladder. The surgical approach is through the usual laparoscopic portals: a primary portal for the optic and two or three secondary portals (5 and 12 mm ) for ancillary instruments. Treatment of the round ligaments and adnexae follows standard hysterectomy technique. The broad ligament and the vesicouterine fold are dissected down to the superior cervix. Prior to applying the electrosurgical loop of the invention, the uterine vessels are dissected and sectioned after occluding them with bipolar coagulation or placement of sutures. Treatment of the uterine arteries in this fashion corresponds to a type III procedure according to the Munro-Parker classification system (see Munro, M. G., Parker, W. H.: A classification for laparoscopic hysterectomy, *Obstetrics and Gynaecology,* 1993; 82: 624–629).

Once the uterine arteries have been cut, it is important to remove any manipulating device that has been placed in the uterus.

The LEC loop according to the present invention is then introduced into the abdominal cavity and placed around the cervix 30 (see FIG. 6). The ends of the loop are firmly held with grasping forceps 31 to form a lasso around the cervix 30 at the level of the isthmus. The uterus 32 is retracted laterally by pulling on the stump of the round ligament 33 in order allow clear vision of the adjacent structures such as bladder, rectum, intestine, etc. (see FIG. 7). Sectioning of the cervix 30 is accomplished by applying high-frequency monopolar current to the electrosurgical LEC loop while it is displaced horizontally. Often it is necessary to pause the section to remove smoke and maintain good vision during amputation. After the cervix has been cut, any residual bleeding may be treated with bipolar coagulation if necessary. The result can be seen in FIG. 8.

At the end of the procedure, the uterine corpus is removed from the abdominal cavity by either morcellation or extraction through a culdotomy incision.

What is claimed is:

1. An electrosurgical cutting apparatus for performing laparoscopic section of an organ, comprising:
    an electrical current transporter, said current transporter comprising;
    a conducting wire;
    electrical insulation portions around said conducting wire at the first end and at the second end, forming respectively a first and a second insulated end and defining a non-insulated cutting portion between said first insulated end and said second insulated end,
    a first fastening device located at said first end of said conducting wire and a second fastening device located at said second end of said conducting wire, said second fastening device being in electrical contact with said conducting wire; and
    a graser for grasping and retaining said first fastening device and/or said second fastening device, the first fastening device and the second fastening device being attachable and detachable from said rasher so that the conducting wire can form a loop when both said first fastening device and said second fastening device are grasped by said grasper.

2. The electrosurgical cutting apparatus as in claim 1, wherein the electrical insulation portions comprise pol (tetrafluoroethylene) and/or medical grade thermoretractable polyolefine.

3. The Electrosurgical cutting apparatus as in claim 1, wherein the conducting wire comprises a metal.

4. The Electrosurgical cutting apparatus as in claim 3, wherein the metal is selected from the group consisting of tungsten and stainless steel.

5. The Electrosurgical cutting apparatus as in claim 1, wherein the conducting wire has a length between 10 and 20 cm.

6. The electrosurgical cutting apparatus as in claim 1, wherein the first fastening device and the second fastening device are clips and the grasper is a standard laparoscopic forceps.

7. The electrosurgical cutting apparatus as in claim 6, firther comprising an insulating tube wherein the standard laparoscopic forceps is slideably moveable within the insulating tube.

8. The electrosurgical cutting apparatus as in claim 1, wherein the first fastening device is a screw and the second fastening device is a conducting sphere.

9. The electrosurgical cutting apparatus as in claim 8, wherein the screw is insulated.

10. The electrosurgical cutting apparatus as in claim 8, wherein the grasper is an introducer device, said introducer device comprising a rod having a proximal end and a distal end, said rod having at its distal end a screwhole adapted to retain said screw and a groove adapted to fit and electrically contact said conducting sphere, said rod having at its proximal end an insulated handle, a contact and an insulated spring therebetween, said contact being in electrical contact with said groove;

the cutting apparatus further comprising an insulated sheath having a length that is greater than the length of the wire and lesser than the length of said introducer device and comprising a tube and a handle, both adapted to fit the introducer, said handle comprising a plug and a contactor mechanism being in electrical contact with each other, said contactor mechanism not being in contact with the contact of the introducer when the introducer is inserted in the sheath and the distal end extends beyond the sheath, and being in contact with the contact of the introducer when the introducer is in a retracted position such that the distal end is inside the sheath, so that the wire and the plug are electrically connected.

11. The Electrosurgical cutting apparatus as in claim 10, further comprising a pin located on the handle of the introducer and a second groove located inside the handle of the sheath, said second groove being adapted to fit said pin and to prohibit translational movement of the introducer with respect to the sheath by trapping said pin when introducer and sheath are rotated with respect to each other.

12. The electrosurgical cutting apparatus as in claim 8, wherein the grasper is an introducer device, said introducer device comprising a rod having a proximal end and a distal end, said rod having at its distal end a screwhole adapted to retain said screw and a groove adapted to fit and electrically contact said conducting sphere, said rod having at its proximal end an insulated handle, an electrical plug and an insulated spring, said electrical plug being in electrical contact with said groove;

the cutting apparatus further comprising an insulated sheath having a length that is greater than the length of the wire and lesser than the length of said introducer device and comprising a tube and a handle, both adapted to fit the introducer.

13. The Electrosurgical cutting apparatus as in claim 12, further comprising a pin located inside the handle of the sheath and a second groove located on the handle of the introducer, said second groove being adapted to fit said pin and to prohibit translational movement of the introducer with respect to the sheath by trapping said pin when introducer and sheath are rotated with respect to each other.

14. A method for performing a laparascopic section of an organ using an electrosurgical cutting apparatus such as in claim 6, comprising the following steps:

grasping one clip of the apparatus with the laparoscopic forceps of the apparatus, introducing the apparatus into a patient's body through a trocar, grasping the second clip of the apparatus with a second standard forceps and placing the conducting wire around the organ to the be sectioned, grasping the second clip of the apparatus with the forceps of the apparatus, and applying high frequency monopolar current to said conducting wire while performing a lateral traction on the apparatus.

15. The method as in claim 14, wherein prior to the introduction of forceps and apparatus into a patient's body through a trocar, the apparatus is inserted in an insulating tube to insulate the apparatus from the trocar.

16. The method as in claim 14, wherein the organ to be sectioned is an uterus.

17. A method for performing a laparoscopic section of an organ using an electrosurgical cutting apparatus as in claim 10, comprising the following steps:

introducing the introducer maximally into the sheath, so that the distal end of the introducer extends beyond the sheath, screwing the screw into the screwhole, pulling the introducer out of the sheath until the wire is completely inside the sheath, introducing said sheath into a patient's body through a trocar, re-introducing the introducer maximally into the sheath, so that the distal end of the introducer extends beyond the sheath and the wire and distal end are in the peritoneal cavity, grasping the sphere of the apparatus with a standard forceps and placing the wire around the organ to be sectioned, introducing the sphere into the groove of the introducer and retracting the introducer until the distal end is inside the sheath, thus preventing the sphere to be released from the groove, rotating the introducer so that introducer and sheath are fixed, and applying high frequency monopolar current to said wire while performing a lateral traction on the apparatus with the introducer and sheath.

18. The method as in claim 17, wherein the organ to be sectioned is an uterus.

19. A method for performing a laparoscopic section of an organ using an electrosurgical cutting apparatus as in claim 12, comprising the following steps:

introducing the introducer maximally into the sheath, so that the distal end of the introducer extends beyond the sheath, screwing the screw into the screwhole, pulling the introducer out of the sheath until the wire is completely inside the sheath, introducing said sheath into a patient's body through a trocar, re-introducing the introducer maximally into the sheath, so that the distal end of the introducer extends beyond the sheath and the wire and distal end are in the peritoneal cavity, grasping the sphere of the apparatus with a standard forceps and placing the wire around the organ to be sectioned, introducing the sphere into the groove of the introducer and retracting the introducer until the distal end is inside the sheath, thus preventing the sphere to be released from the groove, rotating the introducer so that introducer and sheath are fixed, and applying high frequency monopolar current to said wire while performing a lateral traction on the apparatus with the introducer and sheath.

20. The method as in claim 19, wherein the organ to be sectioned is an uterus.

* * * * *

UNITED STATES PATENT AND TRADEMARK OFFICE
CERTIFICATE OF CORRECTION

PATENT NO. : 6,176,858 B1
DATED : January 23, 2001
INVENTOR(S) : Dequesne et al.

It is certified that error appears in the above-identified patent and that said Letters Patent is hereby corrected as shown below:

<u>Column 8, claim 1</u>,
Line 42, "a graser for grasping…" should read -- a grasper for grasping… --
Line 45, "detachable from said rasher…" should read -- detachable from said grasper… --

Signed and Sealed this

Eighth Day of January, 2002

Attest:

JAMES E. ROGAN
*Attesting Officer*   *Director of the United States Patent and Trademark Office*